United States Patent [19]

Breskman

[11] 4,265,887

[45] May 5, 1981

[54] COMPOSITION AND METHOD FOR TREATMENT OF HEMORRHOIDS

[76] Inventor: Joseph S. Breskman, 733 Spring Mill Rd., Villanova, Pa. 19085

[21] Appl. No.: 102,475

[22] Filed: Dec. 11, 1979

[51] Int. Cl.³ .................. A61K 31/44; A61K 31/68; A61K 31/195; A61K 31/525

[52] U.S. Cl. ........................... 424/201; 424/93; 424/106; 424/252; 424/255; 424/263; 424/267; 424/319; 424/329; 424/343

[58] Field of Search ............ 424/201, 93, 106, 252, 424/255, 263, 267, 319, 329, 343

[56] References Cited

U.S. PATENT DOCUMENTS

| | | | |
|---|---|---|---|
| 2,816,854 | 12/1957 | Gross | 424/201 |
| 2,835,627 | 5/1958 | Conine et al. | 424/201 |
| 2,850,429 | 9/1958 | Guleisch et al. | |
| 2,874,089 | 2/1959 | Zuck | 424/201 |
| 2,887,437 | 5/1959 | Klioze et al. | 424/201 |
| 2,901,396 | 8/1959 | Lewis et al. | 424/201 |
| 3,160,564 | 12/1964 | Hanus | 424/201 |
| 3,168,440 | 2/1965 | Meyer | 424/201 |
| 3,175,483 | 3/1965 | Koff et al. | 424/201 |
| 3,826,834 | 7/1974 | Reiches | 424/263 |
| 4,006,219 | 2/1977 | Upham et al. | 424/94 |
| 4,048,316 | 9/1977 | Penn | 424/251 |
| 4,115,576 | 9/1978 | Penn | 424/251 |

FOREIGN PATENT DOCUMENTS

793808 9/1968 Canada ................................. 424/201

OTHER PUBLICATIONS

Handbook of Non-Prescription Drugs, 5th Ed., 1978, pp. 63, 69, 152-155.
The Hemopoietic Vitamin-J. Lab. Clin. Med., pp. 893-900, Jun. 1978.
Reversible Morphological Changes of Rectal Mucosa in Vitamin B12 Deficiency-Path. Res. Pract., 163, 261-266, (1978).

*Primary Examiner*—Douglas W. Robinson
*Attorney, Agent, or Firm*—Steele, Gould & Fried

[57] ABSTRACT

A composition and a method for treatment of hemorrhoids are disclosed. The composition comprises a combination of thiamin, riboflavin, pyridoxine, cobalamin, niacinamide, and pantothenic acid, preferably in liquid form. In preferred embodiments, the composition may also contain whole liver and/or yeast or their extracts. The method comprises oral administration of the composition to a person suffering from hemorrhoids.

5 Claims, No Drawings

COMPOSITION AND METHOD FOR TREATMENT OF HEMORRHOIDS

BACKGROUND OF THE INVENTION

Hemorrhoids are anorectal swellings composed of varicosities of one or more veins in and around the rectal opening. Stretching of the rectal muscular wall during a bowel movement, particularly during constipation, results in repeated stretching of the thin walls of the veins in the rectal area. This repeated stretching may weaken the veins, and result in permanent stretching and stressing of the veins to form hemorrhoids. Once hemorrhoidal conditions become established, the condition usually becomes more acute because the stool is forced through the rectal canal so that it pushes the already swollen veins outward, stretching them even more. The bulging veins may become prolapsed, descending below the anorectal line and outside the anal sphincter. The prolapsed veins may become thrombosed with blood clots and further distend the hemorrhoidal vein, to produce excrusiating pain and exquisite tenderness.

Prolapsed hemorrhoids are quite painful and remain so until the prolapse is reduced. Bleeding frequently occurs with hemorrhoids. Depending on the severity of the hemorrhoidal condition, difficulty may be encountered in sitting and walking.

Typical treatment of hemorrhoids is nonspecific, tending to deal only with the symptoms of pain, itching, bleeding and inflammation. Surgical procedures are resorted to for the most critical conditions. Corrective treatment frequently involves improvement of bowel function through administration of mild laxatives and/or stool softeners to reduce constipation.

A myriad of compositions for local, topical application said to be useful for providing symptomatic relief of hemorrhoids are available commercially. Persons suffering from hemorrhoids usually self-medicate with these products, and may often fail to seek medical advice. The compositions available usually comprise combinations of local anesthetics, vasoconstrictors, antiseptics, and astringents. These compositions are all applied topically, and there is no known oral medication for treatment of hemorrhoids save oral medication taken for relief of severe pain. Such compositions are variably effective in relieving symptoms of hemorrhoids, and may cause some local reactions depending on their chemical composition and skin sensitivity.

Thus, there exists a great need for an improved and effective treatment of hemorrhoids. The need is even greater for a treatment which will not only relieve the symptoms of hemorrhoids, but also remedy the diseased condition. The need for a composition which can be orally administered for treatment of hemorrhoids is especially great, and is provided by this invention.

SUMMARY OF THE INVENTION

A composition and a method for treatment of painful, prolapsed hemorrhoids are provided by this invention. More specifically, a composition comprising a combination of ingredients, which when orally administered to a person suffering from hemorrhoids results in prompt reduction or elimination of hemorrhoidal symptoms is provided by the invention.

The composition includes thiamin, riboflavin, pyridoxine, cobalamin, niacinamide, and pantothenic acid. The composition may additionally include choline, inositol, and whole liver or its fractions or yeast or its fractions. The composition is usually administered in liquid form, however, it may be prepared in tablet or capsule form, or as a slurry or liquid suspension.

The method comprises orally administering an effective amount of the composition to a person suffering with the symptoms of hemorrhoids.

DETAILED DESCRIPTION OF THE INVENTION

It has been discovered that a composition comprising thiamin, riboflavin, pyridoxine, cobalamin, niacinamide, and pantothenic acid is effective in treating the symptoms of hemorrhoids when administered orally. In preferred embodiments, the composition may optionally contain whole liver and/or yeast or their extracts.

As used in the specification and claims of this invention, thiamin is intended to represent vitamin $B_1$, or thiamin as the hydrochloride or other acceptable salts. Riboflavin is intended to represent vitamin $B_2$. Pyridoxine is intended to represent vitamin $B_6$ or pyridoxal, pyridoxal hydrochloride or other acceptable salts. Cobalamin is intended to represent vitamin $B_{12}$ or cyanocobalmin or other acceptable salts. Niacinamide, or nictotinamide, is preferred for use in the composition although an equivalent amount of nicotinic acid could be substituted for this component of the composition. The components of the composition of this invention are each well known and available commercially.

The composition of the invention may optionally include choline or its derivatives such as choline dihydrogen citrate or choline bitartrate, inositol (cyclohexanehexols), and whole liver or its fractions and/or yeast or its fractions.

There are standards which set forth the recommended daily allowance for the individual components of the composition for treatment of vitamin deficiencies. It is known that persons may intake quantities substantially in excess of the recommended daily allowance of the components without harm. The composition for the treatment of hemorrhoids of this invention broadly comprises: thiamin 1 to 15 mg, riboflavin 1 to 10 mg, pyridoxine 0.1 to 33 mg, cobalamin 1 to 30 mcgm, niacinamide 6 to 100 mg, and pantothenic acid 1 to 50 mg. Preferred compositions of the invention comprise thiamin 1 to 5 mg, especially 2.25 mg, riboflavin 1 to 4 mg, especially 2.6 mg, pyridoxine 0.1 to 15 mg, especially 3 mg, cobalamin 1 to 15 mcgm, especially 9 mcgm, niacinamide 4 to 50 mg, especially 30 mg, and pantothenic acid 1 to 25 mg, especially 15 mg. The compositions of the invention may also optionally include 5 to 250 mg choline, 2 to 50 mg inositol and a member selected from the group consisting of whole liver or its fractions and yeast or its fractions 250 to 300 mg.

The compositions of this invention are to be administered orally, and preferably are administered in liquid form. Alternatively, the composition could be administered in the form of tablets, capsules, liquid suspensions, and the like through the expediency of formulation with well known and accepted pharmaceutical carriers. The method of the invention involves the oral administration of an amount of the composition effective to impart relief from hemorrhoidal symptoms and to maintain a symptom free condition in a person suffering with hemorrhoids. Initial treatment for acute conditions may involve administration of eight times more of the composition than is required for maintenance after the acute symptoms have subsided.

The precise mechanism by which the composition of this invention achieves the unexpected and surprising treatment of hemorrhoids is not known with certainty. It is theorized, however, that the composition may have a nutritional interrelationship and a biochemical influence on the mucosal surfaces of the rectal area, especially with varicosities associated with hemorrhoids. It is also conceivable that engorgement, enlargement and thinning of the walls of hemorrhoidal veins may have a relationship with liver abnormalities not unlike that of esophageal varicies. Again, there may be a nutritional interrelationship between the composition and liver abnormalities which plays a role in amelioration of hemorrhoid symptoms. The composition may also affect bulking and stool softening and decrease constipation, all of which may have a bearing on its ability to provide relief from symptoms of hemorrhoids. These beneficial effects are demonstrated by the following tests.

EXAMPLE 1

Twenty-four persons experiencing symptoms of acute hemorrhoidal pain were informed they could avail themselves of a liquid medication comprising a combination of vitamins and nutrients which had successfully ameliorated the symptoms of hemoroidal pain. These patients were orally administered a liquid composition containing 6.75 mg thiamin, 7.8 mg riboflavin, 9 mg pyridoxine, 27 mcgm cobalamin, 90 mg niacinamide, and 45 mg pantothenic acid four times a day for two days followed by oral administration of a liquid composition containing 3.35 mg thiamin, 3.9 mg riboflavin, 4.5 mg pyridoxine, 13.5 mcgm cobalamin, 45 niacinamide, and 22.5 mg pantothenic acid two times a day for four days. Of the 24 persons receiving treatment, 14 reported moderate to severe painful hemorrhoids on initiation of treatment. Of these 14 persons, nine reported prompt and excellent improvement with lessening of pain and tenderness to the rectal areas and a decrease in the size and swelling of hemorrhoids. Two persons reported they were "somewhat improved", while three reported no significant benefits from the treatment. One person with very enlarged and distended hemorrhoids experienced significant lessening of pain and discomfort within one day.

EXAMPLE 2

The evaluation of Example 1 was repeated in another study involving 17 persons suffering with hemorrhoids who were treated with the liquid composition according to the regimen described in Example 1. Of the 17 persons receiving treatment, 11 persons reported prompt and excellent improvement, particularly those who had the most severe symptoms of pain, bleeding and itching. Two persons reported that there was no improvement noted with the treatment, two others reported that the treatment was not effective, but described the undesired symptoms as disappearing, and an additional two persons reported no improvement, but had only slight symptoms of hemorrhoids prior to treatment.

The foregoing examples are illustrative of the preferred embodiments of the invention, and should not be considered as limiting the scope of the invention. The evaluations reported in the foregoing examples were completed by physicians at the request of the inventor who advised the physicians of his personal experience with the composition of this invention. The inventor had determined by personal experience and observation over a number of years, the surprising and remarkable curing effect of the composition on hemorrhoidal symptoms. Despite initial skepticism concerning use of an orally administered composition for hemorrhoid treatment, the physicians' evaulations as set forth in Examples 1 and 2, confirm the inventor's experience of successful treatment of hemorrhoids with the composition and method defined in the appended claims.

Having thus described the invention,

What is claimed is:

1. A method of treatment of hemorrhoids which comprises orally administering to a person suffering with hemorrhoids a composition comprising:

| | |
|---|---|
| Thiamin | 1 to 15 mg |
| Riboflavin | 1 to 10 mg |
| Pyridoxine | 0.1 to 33 mg |
| Cobalamin | 1 to 3 mcgm |
| Niacinamide | 6 to 100 mg |
| Pantothenic Acid | 1 to 50 mg | in an amount effective to impart relief from hemorrhoidal symptoms and to maintain a symptom free condition in a person suffering with hemorrhoids.

2. The method of claim 1 wherein the composition comprises:

| | |
|---|---|
| Thiamin | 1 to 5 mg |
| Riboflavin | 1 to 4 mg |
| Pyridoxine | 0.1 to 15 mg |
| Cobalamin | 1 to 15 mcgm |
| Niacinamide | 6 to 50 mg |
| Pantothenic Acid | 1 to 25 mg. |

3. The method of claim 2 wherein the composition comprises:

| | |
|---|---|
| Thiamin | 2.25 mg |
| Riboflavin | 2.6 mg |
| Pyridoxine | 3 mg |
| Cobalamin | 9 mcgm |
| Niacinamide | 30 mg |
| Pantothenic Acid | 15 mg. |

4. The method of claim 1 wherein the composition comprises:

| | |
|---|---|
| Thiamin | 1 to 15 mg |
| Riboflavin | 1 to 10 mg |
| Pyridoxine | 0.1 to 33 mg |
| Cobalamin | 1 to 30 mcgm |
| Niacinamide | 6 to 100 mg |
| Pantothenic Acid | 1 to 50 mg |
| Choline | 5 to 250 mg |
| Inositol | 2 to 50 mg, |
| and a member selected from the group consisting of whole liver or its fractions and yeast or its fractions | 250 to 300 mg. |

5. The method of claim 1 wherein the composition is administered in an amount of 6.75 mg thiamin, 7.8 mg riboflavin, 9 mg pyridoxine, 27 mcgm cobalamin, 90 mg niacinamide, and 45 mg pantothenic acid four times a day for two days followed by 3.35 mg thiamin, 3.9 mg riboflavin, 4.5 mg pyridoxine, 13.5 mcgm cobalamin, 45 mg niacinamide and 22.5 mg pantothenic acid two times a day for four days.

* * * * *

UNITED STATES PATENT AND TRADEMARK OFFICE
CERTIFICATE OF CORRECTION

PATENT NO. : 4,265,887
DATED : May 5, 1981
INVENTOR(S) : Joseph S. Breskman

It is certified that error appears in the above-identified patent and that said Letters Patent are hereby corrected as shown below:

Claim 1, line 7     Cobalamin     1 to 3 mcgm
        should be     Cobalamin     1 to 30 mcgm Signed and Sealed this Twenty-fifth Day of August 1981

[SEAL]

Attest:

GERALD J. MOSSINGHOFF

Attesting Officer     Commissioner of Patents and Trademarks